US006616688B2

(12) United States Patent
Von Oepen

(10) Patent No.: US 6,616,688 B2
(45) Date of Patent: Sep. 9, 2003

(54) STENT

(75) Inventor: Randolph Von Oepen, Hirrlingen (DE)

(73) Assignee: Jomed Implantate GmbH, Rangendingen (DE)

( * ) Notice: Subject to any disclaimer, the term of this patent is extended or adjusted under 35 U.S.C. 154(b) by 0 days.

(21) Appl. No.: 09/909,754

(22) Filed: Jul. 23, 2001

(65) Prior Publication Data
US 2001/0041929 A1 Nov. 15, 2001

Related U.S. Application Data

(63) Continuation of application No. 09/379,586, filed on Aug. 24, 1999, now Pat. No. 6,264,690.

(51) Int. Cl.⁷ .................................................. A61F 2/06
(52) U.S. Cl. ...................... 623/1.15; 623/903; 623/1.3
(58) Field of Search ................................ 623/1.15, 1.3, 623/1.31, 1.35, 1.37, 1, 903

(56) References Cited

U.S. PATENT DOCUMENTS

| 5,141,516 A | 8/1992 | Detweiler |
| 5,476,506 A | 12/1995 | Lunn |
| 5,609,605 A | 3/1997 | Marshall et al. |
| 5,728,104 A | 3/1998 | Trotta |
| 5,807,327 A | 9/1998 | Green et al. |
| 5,836,966 A | 11/1998 | St. Germain |
| 5,906,641 A | 5/1999 | Thompson et al. |
| 6,010,529 A | 1/2000 | Herweck et al. |
| 6,027,517 A | 2/2000 | Crocker et al. |
| 6,027,526 A * | 2/2000 | Limon et al. ............... 623/1.15 |
| 6,076,529 A | 6/2000 | Vanney et al. |
| 6,193,747 B1 * | 2/2001 | Von Oepen ................. 623/1.15 |
| 6,264,690 B1 * | 7/2001 | Von Oepen ................... 623/1.3 |
| 6,325,825 B1 * | 12/2001 | Kula et al. .................... 623/1.3 |

* cited by examiner

Primary Examiner—David H. Willse
Assistant Examiner—Suzette Jackson
(74) Attorney, Agent, or Firm—Shinjyu Global IP Counselors, LLP

(57) ABSTRACT

A stent is a device that is adapted to be implanted into narrowed portions of hollow vessels of a body. The stent (1) comprises a stent body (2) that has at least two different wall thicknesses ($W_E$, $W_H$). The different wall thicknesses result in different flexibility characteristics of the stent in the longitudinal direction. Thus the stent according to the invention prevents irritations of the wall of the vessel in the area of the implanted stent, whereby the risk of restenosis in said area can be reduced considerably.

27 Claims, 5 Drawing Sheets

STENT

CROSS-REFERENCE TO RELATED APPLICATIONS

This application is a continuation application of U.S. patent application Ser. No. 09/379,586 filed on Aug. 24, 1999, now U.S. Pat. No. 6,264,690. The entire disclosure of U.S. patent application Ser. No. 09/379,586 is hereby incorporated herein by reference.

BACKGROUND OF THE INVENTION

1. Field of the Invention

This invention generally relates to a stent. More specifically, the present invention relates to a stent comprising a stent body which is in particular used for expanding narrowed hollow vessels.

2. Background Information

Different types of stents are known from the prior art. These stents form a vascular prosthesis made from a physically compatible material. Stents are in general used for expanding hollow vessels, such as blood vessels or body orifices, and for keeping the vessels or orifices in an expanded state. To this end, the stent is normally positioned in its non-expanded state within a patient's body inside a narrowed hollow vessel and is then expanded by suitable means, for instance a balloon catheter. The stent body normally consists of a web structure, which comprises a plurality of neighboring cells, each cell being defined by webs. During expansion the individual web portions of the stent are deformed, so that the portions permanently remain in the expanded form.

The problem of restenosis often arises in such expanded hollow vessels. After some time the portion of the hollow vessel which has been expanded by the stent is narrowed again. Such a restenosis may, inter alia, be caused by the inherent stiffness of the stent. As schematically shown in FIG. 6, the hollow vessel 10 is stiffened by the stent 1'. Strong irritations R of the vessel wall which result in a restenosis of the hollow vessel can in particular be observed on the two end portions of the stent due to the inherent stiffness of the stent body 2'.

In view of the above, there exists a need for a stent which overcomes the above mentioned problems in the prior art. This invention addresses this need in the prior art as well as other needs, which will become apparent to those skilled in the art from this disclosure.

SUMMARY OF THE INVENTION

One object of the present invention is to provide a stent that reduces the risk of restenosis in a hollow vessel in the area of an implanted stent.

Hence, according to the invention, there is provided a stent the wall thickness of which has been changed. This results in a stent having portions that due to the different wall thicknesses exhibit different inherent stiffnesses. Hence, the stent body within the portions of a reduced wall thickness has an increased flexibility, whereby irritations of the vessel wall at these places can be reduced or even be prevented altogether. Hence, the risk of restenosis in these portions can be reduced considerably.

Preferably, the wall thickness of the two end portions of the stent body is smaller than the wall thickness of a main portion of the stent body. As a consequence, the inherent stiffness of the two end portions of the stent body can in particular be reduced, so that the end portions exhibit an increased flexibility, whereby an abrupt "directional change" or a bending of the hollow vessel due to a different stiffness degree between the portion of the hollow vessel without stent and the portion of the hollow vessel with stent can be prevented. As a result, one obtains a more gentle transition between the hollow vessel and the stent, whereby a strong irritation on the end portions of the stent can be avoided.

According to a preferred embodiment of the present invention, the stent body comprises exactly one end portion having a smaller wall thickness than the remaining portion of the stent body. Such a stent can preferably be used in branches or rami of hollow vessels. The stent is arranged in the branched portion such that the end portion of a reduced wall thickness is oriented away from the branched portion. Hence, the stent portion is provided in the area of the branched portion or directly next to the branched portion with an increased wall thickness because the risk of irritations created by the stent is small on account of the natural extension of the branched portion in said area. In the area that is more remote from the branched portion, the stent, however, has a smaller wall thickness so that an increased flexibility of the stent is observed in said area and the stent can follow the natural course of the hollow vessel. Hence, the risk of irritations is reduced thanks to the high flexibility of the end portion of the stent.

To achieve a defined transition between the main portion and the end portion, which has a reduced wall thickness, the transition between said two portions is stepped or graded. As a result, the stiffness of the stent can be changed abruptly and the desired flexibility of the stent can be obtained in defined portions of the stent body.

To attain a gradual change in the stiffness or flexibility, respectively, of the stent body, the transition between the portion of an increased wall thickness to the portion of a reduced wall thickness is made continuous. The transition between the two wall thicknesses may e.g. be configured such that it is linear or exhibits a gradually changing increase.

To provide different inherent stiffnesses of the two end portions of the stent body, the wall thicknesses of the two end portions may be different. To provide a symmetrical stent, the end portions of the stent body may also have identical wall thicknesses. Furthermore, flexible end portions may also be achieved by identical or different lengths of the end portions in the axial direction or, in the case of gradually changing wall thicknesses in the transitional portion, by different axial lengths of the transitional portions.

These and other objects, features, aspects and advantages of the present invention will become apparent to those skilled in the art from the following detailed description, which, taken in conjunction with the annexed drawings, discloses preferred embodiments of the present invention.

BRIEF DESCRIPTION OF THE DRAWINGS

Referring now to the attached drawings which form a part of this original disclosure.

DETAILED DESCRIPTION OF THE PREFERRED EMBODIMENTS

Figure 1:
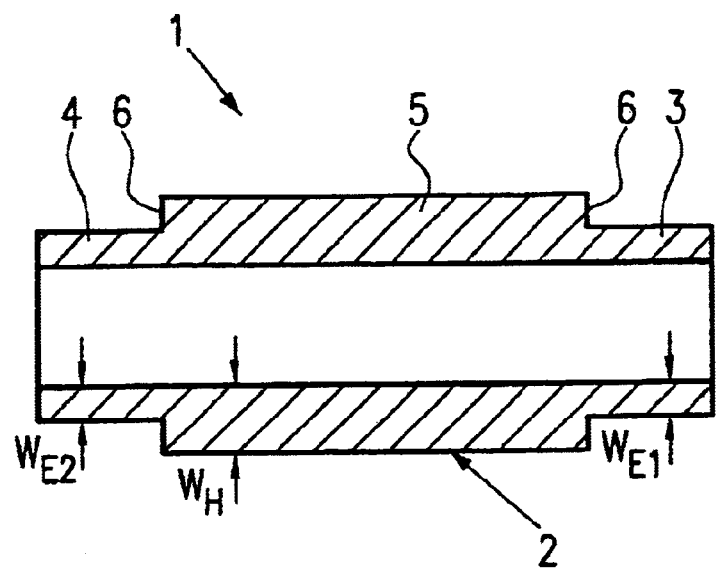
FIG. 1 is a schematic cross-sectional view of a stent in the longitudinal direction according to a first embodiment of the present invention.
Figure 1A:
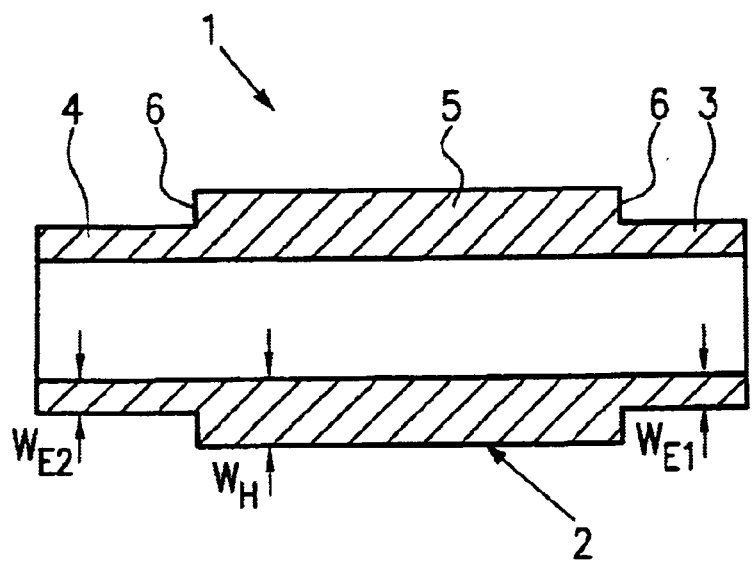
FIG. 1A is a schematic cross-sectional view of a stent in the longitudinal direction according to a second embodiment of the present invention.
Figure 5:
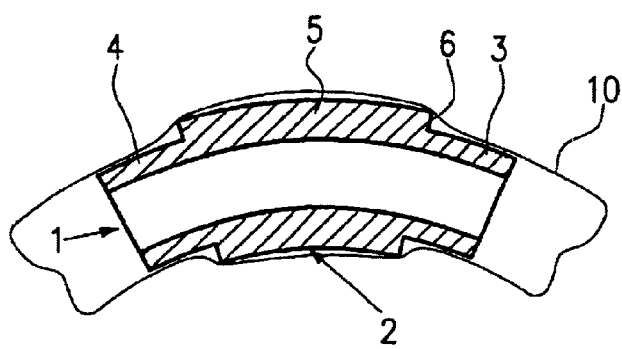
FIG. 5 is a schematic cross-sectional view showing the arrangement of a stent according to the first embodiment in a hollow vessel.

Referring initially to FIGS. 1, 1A and 5, a stent 1 in accordance with two embodiments of the present invention is illustrated. Since the second embodiment of FIG. 1A is substantially identical to the first embodiment, similar parts of the stents are designated by the same reference numerals. Preferably, the stent 1 consists of a substantially cylindrical stent body, which is made hollow in its interior to enable fluid to pass therethrough. The stent body 2 consists of a flexible web structure, which is not shown for the sake of clarity. Rather, the stent body 2 will be illustrated as a solid tube for the sake of clarity.

Figure 1B:
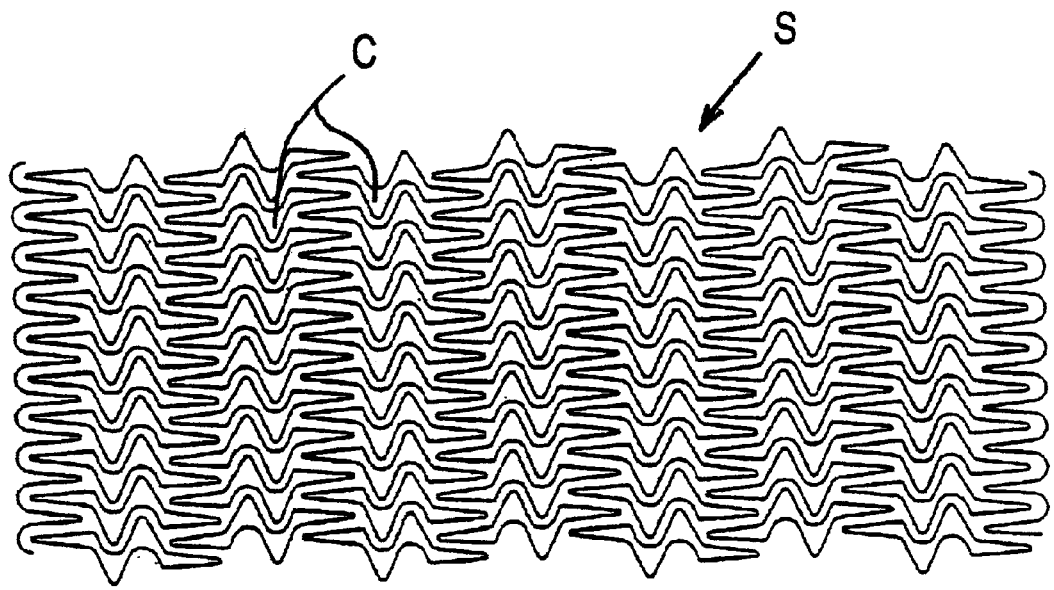
FIG. 1B is a side view of a web structure of a plurality of neighboring cells that form the main portion and end portions of the stent body that is schematically illustrated in FIGS. 1 and 1A.
Figure 1C:
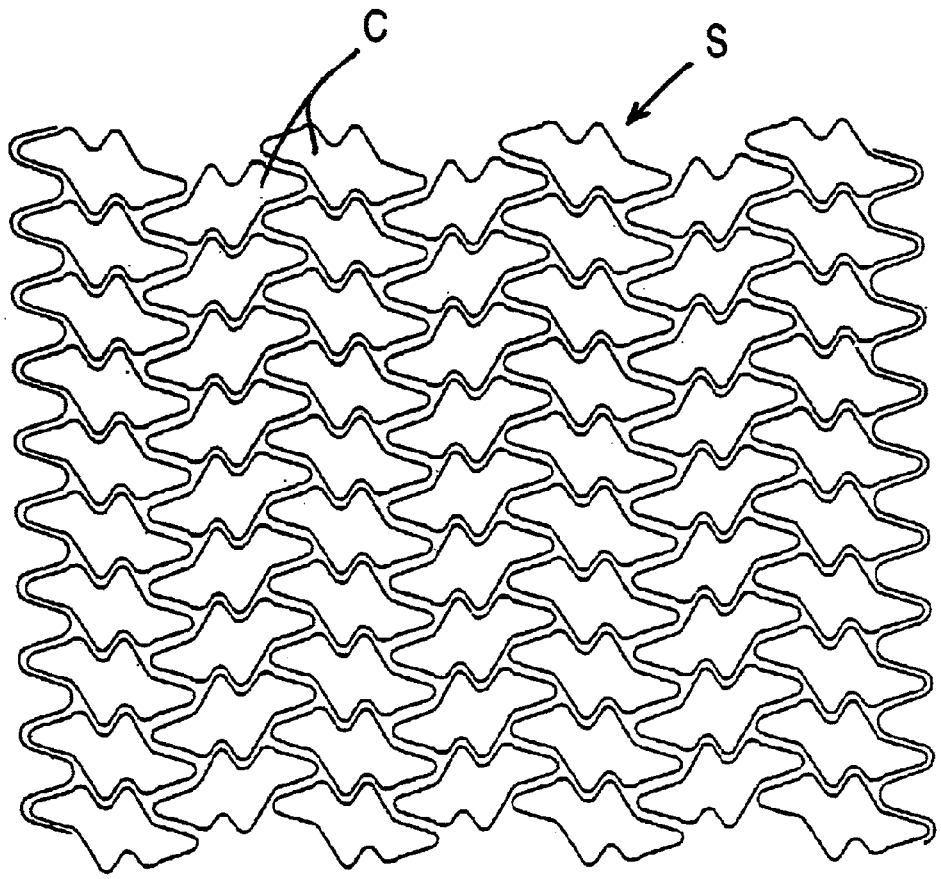
FIG. 1C is a side view of the web structure illustrated in FIG. 1B after being expanded.

Basically, the flexible web structure of the stent body 2 is used for expanding hollow vessels, such as blood vessels or body orifices, and for keeping the vessels or orifices in an expanded state. To this end, the stent body 2 is normally positioned in its non-expanded state within a patients body inside a narrowed hollow vessel. Then the stent body 2 is expanded by suitable means, for instance by a balloon catheter. As seen in FIGS. 1B and 1C, the stent body 2 normally consists of a web structure 5, which comprises a plurality of neighboring cells each cell C being defined by webs. For example, the web structure S of the stent body 2 can be constructed in a manner that is similar to the web structure disclosed in U.S. Pat. No. 6,193,747, filed on Oct. 16, 1998, e.g., see the web structure shown in FIGS. 3 and 4 of U.S. Pat. No. 6,193,747. The entire disclosure of U.S. Pat. No. 6,193,747 is hereby incorporated herein by reference. Of course, other types of known web structures can be used, and thus, modified in accordance with the present invention. During expansion the individual web portions of the stent body 2 are deformed, so that the web portions permanently remain in the expanded form as seen in FIG. 1C. The flexible web structure S of the stent body 2 is well known in the art, and thus, it will not be discussed in detail herein.

Figure 2:
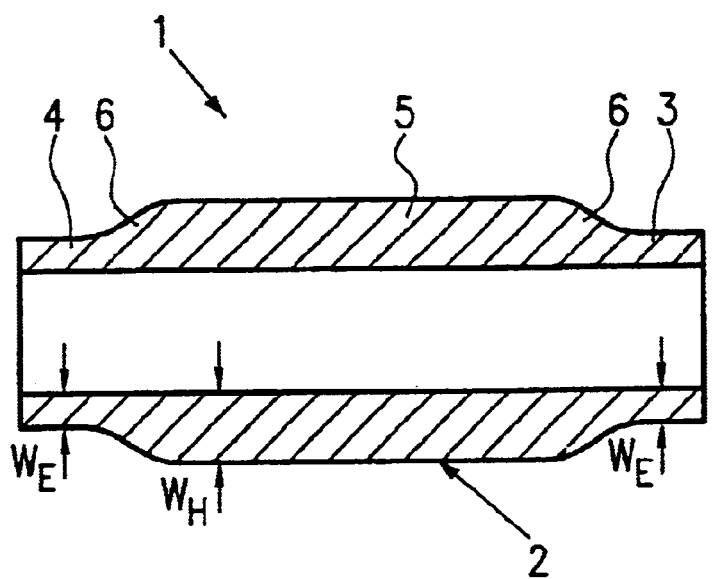
FIG. 2 is a schematic cross-sectional view of a stent in the longitudinal direction according to a third embodiment of the present invention.
Figure 2A:
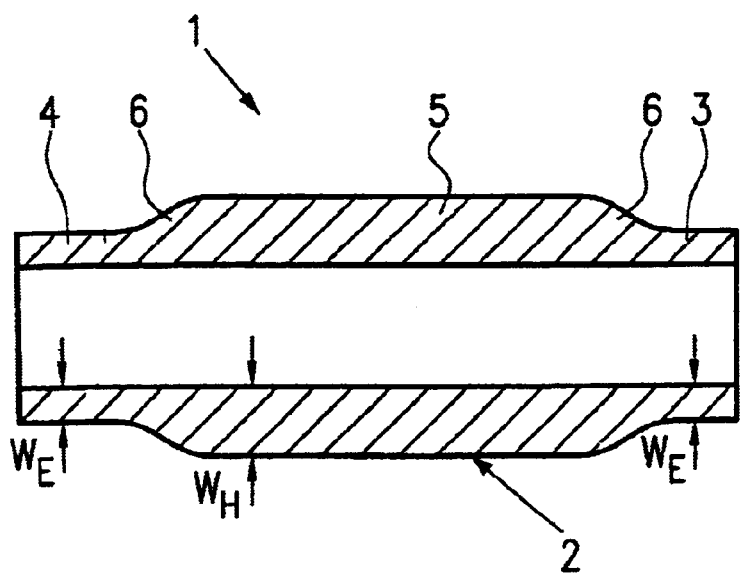
FIG. 2A is a schematic cross-sectional view of a stent in the longitudinal direction according to a fourth embodiment of the present invention.
Figure 3:
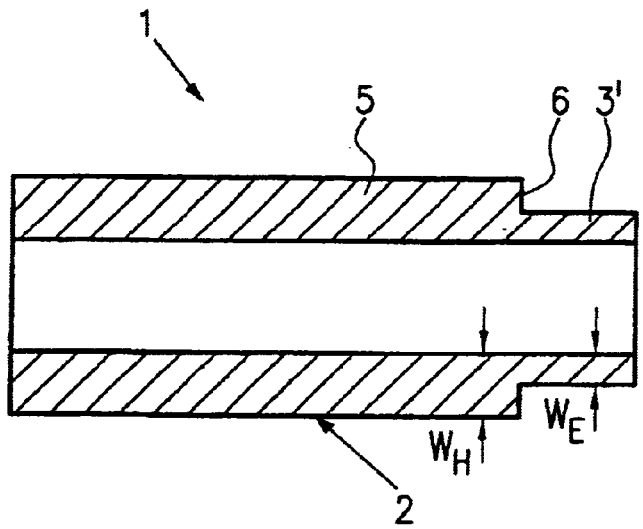
FIG. 3 is a schematic cross-sectional view of a stent in the longitudinal direction according to a fifth embodiment of the present invention.

As seen in FIG. 1, the stent body 2 of the first embodiment is subdivided into three portions, namely a main or center portion 5, a first end portion 3 and a second end portion 4. The stent body 2 has a constant inner diameter along its entire axial length of the portions 3, 4, and 5 (FIGS. 1, 1A, 2, 2A, 3 and 3A). The portions 3, 4, and 5 of the stent body 2 have a web structure, such the web structure S as seen in FIGS. 1B and 1C. In this embodiment, only the thicknesses of the portions 3, 4, and 5 of the stent body 2 are different. The web structure S is formed of the plurality of neighboring cells C. The web structure S of the main or center portion 5 includes a plurality of first cells, while each of the first and second end portions 3 and 4 includes at least one second cell (more preferably a plurality of second cells). In any event, the web structure S of the second cells of the first and second end portions 3 and 4 preferably have a different wall thickness than the web structure of the first cells as seen in FIGS. 1–3 such that the main or center portion 5 is thicker than one or both of the end portions 3 and 4.

In the first, second, third and fourth embodiments of the present invention (FIGS. 1, 1A, 2 and 2A), the second cells are disposed in the main portion 5, while the first cells are disposed in the first and second end portions 3 and 4. Thus, the wall thickness formed by the web structure S of the second cells is a greater wall thickness than the wall thickness formed by the web structure S of the end portions 3 and 4. Alternatively, as seen in the fifth and sixth embodiments of the present invention (FIGS. 3 and 3A), the neighboring cells disposed in the second end portion 4 and the main portion 5 comprise the second cells, while the first cells are disposed in the first end portion 3.

A transition is formed between the first cells disposed in the first and second end portions 3 and 4 and the second cells disposed in the main portion 5. This transition can be stepped (FIGS. 1 and 1A) or continuously tapered (FIGS. 2 and 2A). The first and second end portions 3 and 4 can have substantially equal longitudinal lengths (FIGS. 1 and 2) or different longitudinal lengths (FIGS. 1A and 2A).

The main portion 5 and the first and second end portions 3 and 4 have arranged therebetween a transition or transitional portion 6 which connects the main portion 5 to the respective end portions 3 and 4. As shown in FIG. 1, the transition 6 from the main portion 5 to the end portions 3 and 4 is stepped or graded. This means that different flexibilities of the respective stent portions are obtained because of the different wall thicknesses of main portion 5 and end portions 3 and 4, resulting in an improved flexibility because of the smaller wall thickness $W_{E1}$ or $W_{E2}$ in the area. Since the transition 6 is configured to be perpendicular to the surface of the end portions 3 and 4 and the main portion 5, respectively, a sudden change in the flexibility of the stent is obtained in this area.

As shown in FIG. 5, a stent of such a design can very easily be adapted to the respective conditions or natural extension of the vessel 10. As becomes also apparent from FIG. 5, the end portions 3 and 4 can be adapted to a relatively strong curvature of the hollow vessel 10. As a consequence, the vessel 10 extends in a uniform manner without any sudden directional changes, i.e. also in the area of the implanted stent. In particular, strong irritations, which are observed in conventional stents, can thus be prevented on the end portions of the stent, whereby the risk of restenosis is considerably reduced.

Figure 6:
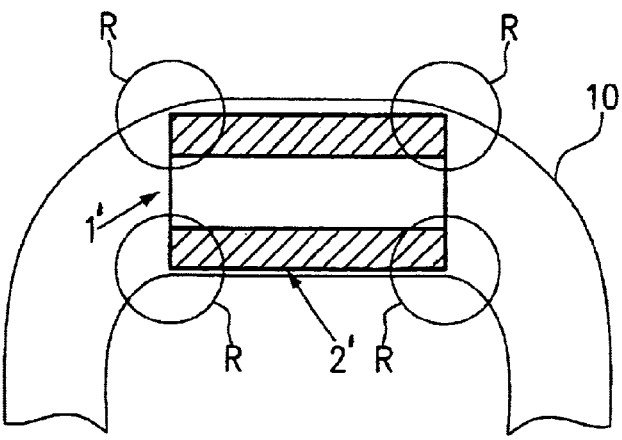
FIG. 6 is a schematic cross-sectional view of a prior art stent located within a hollow vessel.

FIG. 6 shows, by way of comparison, a standard or prior art stent 1', which has been implanted into a hollow vessel 10. Since the stent body 2' of the stent has a uniform wall thickness, points or places R which are subjected to strong irritations are observed on the end portions of the stent 1', in particular in the case of the hollow vessel 10 extending in bent fashion. Such irritations R may be responsible for restenosis, and thus for a narrowing of the hollow vessel 10, which means that a so-called restenosis is observed in the area of the implanted stent.

Thanks to the end portions 3 and 4 of the stent 1, which are made flexible according to the invention, such points or places R of considerable irritation can be avoided, since the whole stent 1 can be adapted to the natural bent course of the hollow vessel 10 on account of the increased flexibility in the end portion. To be more specific, a sudden change in stiffness which is normally observed between the hollow vessel 10 and the portion of the hollow vessel that is provided with the stent is consequently weakened or attenuated by the flexible ends. Hence, restenosis caused by irritations on account of the implanted stent can be reduced in an efficient manner.

Third and Fourth Embodiments

FIGS. 2 and 2A show third and fourth embodiments of a stent 1 according to the present invention. Corresponding or identical parts of these stents are designated by the same reference numerals as used in the first embodiment. The stent 1 has a tubular stent body 2, which consists of a main portion 5 and two end portions 3 and 4. The wall thickness $W_E$ of the end portions 3 and 4 is about half the size of the wall thickness $W_H$ of the main portion 5. The main portion 5 is connected to the end portions 3 and 4 via a respective transition or transitional portion 6. The transition 6 is designed such that a continuously extending transition is obtained between main portion 5 and end portions 3 and 4 (cf. FIG. 2). Starting from the end portions 3 and 4, the wall thickness of the stent body 2 increases towards the main portion 5. As a result of such a gradual increase in the wall thickness from the end portion to the main portion, the flexibility of the stent 1 is also changed in this portion. This means that the flexibility of the transitional portion 6 is reduced from the end portion towards the main portion. In contrast to the first embodiment, there is no abrupt change in flexibility and no sudden change in the inherent stiffness of the stent in the transitional portion, but the stiffness changes slowly and continuously in the transition 6.

Hence, the stent 1 of this embodiment exhibits an increased flexibility in the end portion of the stent 1, whereby restenosis caused by irritations due to the implanted stent is prevented in an efficient manner. In addition, the transition 6 between the end portions 3 and 4 and the main portion 5 can be designed in response to the desired requirements in such a manner that the flexibility of the transition 6 is changed progressively or stepwise. The transition 6 may be designed in any desired manner. For instance, a linear or parabolic transition 6 may be provided for, or a transition 6 including a plurality of small steps. In the illustrated embodiments of FIGS. 2 and 2A, transition 6 forms a conical outer surface between the main portion 5 and each of the end portions 3 and 4.

Fifth and Sixth Embodiments

Figure 3A:
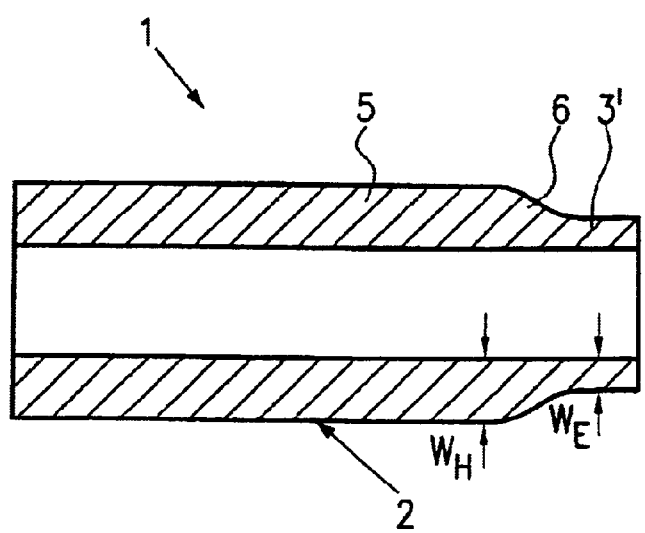
FIG. 3A is a schematic cross-sectional view of a stent in the longitudinal direction according to a sixth embodiment of the present invention.
Figure 4:
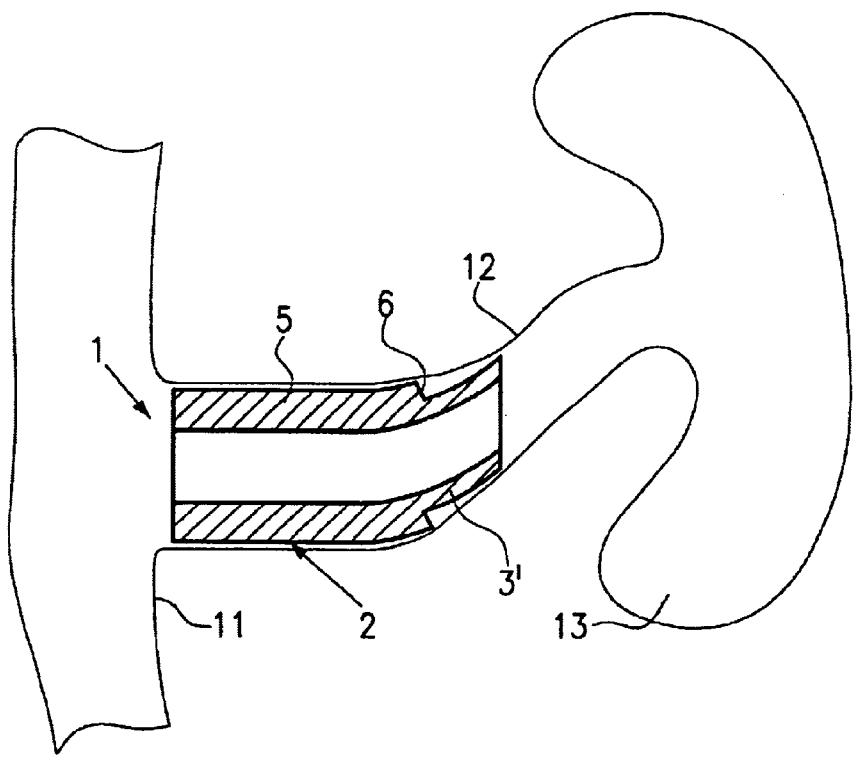
FIG. 4 is a schematic cross-sectional view showing an arrangement of the stent according to the fifth embodiment of the present invention in a branched portion of a hollow vessel.

FIGS. 3 and 4 show a fifth embodiment of a stent according to the present invention, while FIG. 3A shows a sixth embodiment of the present invention. Corresponding or identical parts of the stent have again been designated by the same reference numerals as used in the prior embodiments. Each of the stents 1 of these embodiments comprises a tubular stent body 2, which has a main portion 5. In contrast to the two preceding embodiments, the stent body 2 of these embodiments have only arranged thereon one end portion 3' with a smaller wall thickness $W_E$ than the main portion 5. The other end of the stent body 2 has the same wall thickness $W_H$ as the main portion 5 (cf. FIG. 3). A transition 6 between the main portion 5 and the end portion 3' can be stepped as in the first embodiment or gradually sloped as in the third and fourth embodiments. Hence, there is a sudden change in the flexibility of the stent body 2 on the transitional portion 6 due to the different wall thicknesses. Of course, the transition 6 may be configured in any desired manner that will still carry out the principles of the present invention.

As shown in FIG. 4, the stent 1 of the fifth embodiment is primarily used on a branches or ramifications of hollow vessels (a treatment site within a patient). Generally speaking, the stent is to delivered to a treatment site within a patient; and then expanded into contact with the treatment site as seen in FIG. 4. FIG. 4 shows, by way of example, a branch or ramus 12 extending from the aorta 11 to the kidney 13. Since the ramus 12 directly next to the place branching from the aorta 11 extends substantially along the branching direction and is devoid of any torsions or curve-like or curved extensions, or the like, the stent body 2 may be given a standard flexibility in said area. As a consequence, the second end of the stent body 2 in the area may have the same wall thickness as the main portion 5 (cf. FIG. 4). The other end portion 3' of the stent body 2 which is oriented towards the kidney 13 is again provided with a smaller wall thickness $W_E$ than the main portion 5, by analogy with the first two embodiments. Hence, the stent 1 can be adapted in an ideal manner to the natural course of the ramus 12 of the hollow vessel, and irritations of the vessel wall can be reduced on the respective end portions of the stent. Since hollow vessels, such as the kidney, are moving on account of inhalation and exhalation processes, the vessel 12 which connects the kidney 13 and the aorta 11 to each other is also moved considerably. In comparison with a conventional stent, the flexibility of the vessel is thus increased considerably by the inventive stent of the third embodiment, and irritations of the wall of the vessel are attenuated. As a consequence, the risk of restenosis in the area of the implanted stent is reduced considerably.

While several embodiments have been chosen to illustrate the present invention, it will be apparent to those skilled in the art from this disclosure that various changes and modifications can be made herein without departing from the scope of the invention as defined in the appended claims. Furthermore, the foregoing description of the embodiments according to the present invention are provided for illustration only, and not for the purpose of limiting the invention as defined by the appended claims and their equivalents.

What is claimed is:

1. A stent apparatus for stenting, comprising:
    a stent body having a web structure with a plurality of neighboring cells, said neighboring cells including a plurality of first cells and at least one second cell,
    said at least one second cell having a different wall thickness than said first cells, a transition being formed between said first cells and said at least one second cell, said transition being stepped, and
    said stent having a constant inner diameter along its length.
2. The stent apparatus of claim 1, wherein
    said stent comprises first and second end portions, and a main portion disposed between said first and second end portions, with said at least one second cell being disposed in said main portion.

3. The stent apparatus of claim 2, wherein
said neighboring cells in said first and second end portions comprise a plurality of first cells.

4. The stent apparatus of claim 2, wherein
said first and second end portions have substantially equal longitudinal lengths.

5. The stent apparatus of claim 2, wherein
said first end portion has a first longitudinal length and said second end portion has a second longitudinal length, said first longitudinal length being different than said second longitudinal length.

6. The stent apparatus of 2, wherein
said different wall thickness of said at least one second cell comprises a greater wall thickness than said first cells.

7. The stent apparatus of claim 2, wherein
said neighboring cells disposed in said main portion comprise a plurality of said second cells.

8. The stent apparatus of claim 7, wherein
said first cells are disposed in said first end portion.

9. The apparatus of claim 7, wherein
said neighboring cells disposed in said main portion comprise a plurality of said second cells.

10. The stent apparatus of claim 9, wherein
said first cells are disposed in said first end portion.

11. A method for stenting comprising:
providing a stent apparatus comprising a stent body having first and second end portions, and a main portion, said main portion having a greater wall thickness than said first end portion, said stent body having a constant inner diameter along its length;
percutaneously delivering said apparatus to a treatment site within a patient; and
expanding said stent apparatus into contact with said treatrent site.

12. The method of claim 11, further comprising
positioning said first end portion to contact a curved section of said treatment site.

13. The method of claim 11, further comprising
positioning said first end portion to contact a branch or ramification of said treatment site.

14. The method of claim 11, further comprising
positioning said stent apparatus in a branch or ramus extending from the aorta to a kidney, and positioning said first end portion closer to said kidney than said main portion.

15. The method of claim 11, further comprising
said main portion has a greater wall thickness than said second end portion, and positioning said first and second end portions to contact curved sections of said treatment site.

16. The method of claim 11, wherein
said providing of said stent apparatus further comprises providing said stent body with a web structure having a plurality of neighboring cells, said cells including a plurality of first cells and at least one second cell with a greater wall thickness than said first cells, said at least one second cell is disposed in said main portion of said stent body.

17. The method of claim 16, further comprising
providing a transition formed between said first cells and said at least one second cell.

18. The method of claim 17, wherein
said providing of said transition further comprises providing a stepped transition.

19. The method of claim 17, wherein
said providing of said transition further comprises providing a continuously tapered transition.

20. The method of claim 17, wherein
said providing of said transition further comprises providing a linearly tapered transition.

21. The method of claim 16, wherein
said neighboring cells in said first and second end portions comprise a plurality of first cells.

22. The method of claim 16, wherein
said neighboring cells disposed in said main portion comprise a plurality of said second cells.

23. The method of claim 22, wherein
said first cells are disposed in said first end portion.

24. The method of claim 22, wherein
said neighboring cells disposed in said second end portion comprise a plurality of said second cells.

25. The method of claim 24, wherein
said first cells are disposed in said first end portion.

26. The method of claim 11, wherein
said first and second end portions have substantially equal longitudinal lengths.

27. The method of claim 11, wherein
said first end portion has a first longitudinal length and said second end portion has a second longitudinal length, said first longitudinal length being different than said second longitudinal length.

* * * * *